United States Patent [19]
Greenberg et al.

[11] Patent Number: 5,767,103
[45] Date of Patent: Jun. 16, 1998

[54] NITRIC OXIDE SEQUESTRANT

[75] Inventors: Stanley S. Greenberg; Jianming Xie; Mark J. S. Miller, all of New Orleans; Judith Zatarian-Kuebel, Mandeville, all of La.

[73] Assignee: Research Corporation Tech., Inc., Tucson, Ariz.

[21] Appl. No.: 244,179

[22] PCT Filed: May 17, 1994

[86] PCT No.: PCT/US94/05650

§ 371 Date: Apr. 19, 1995

§ 102(e) Date: Apr. 19, 1995

[87] PCT Pub. No.: WO95/31204

PCT Pub. Date: Nov. 23, 1995

[51] Int. Cl.$^6$ ................................................. A61K 31/70
[52] U.S. Cl. .................................................. 514/52
[58] Field of Search .................................... 514/52

[56] References Cited

U.S. PATENT DOCUMENTS

| | | | |
|---|---|---|---|
| 5,084,482 | 1/1992 | Hirsch et al. | 514/562 |
| 5,317,040 | 5/1994 | Goldman | 514/634 |
| 5,480,866 | 1/1996 | Bonaventura et al. | 514/6 |

FOREIGN PATENT DOCUMENTS

| | | |
|---|---|---|
| 9054534 | 4/1990 | Australia . |
| 9169487 | 1/1991 | Australia . |

OTHER PUBLICATIONS

J.A. Lorente, et al. "L-arginine Pathway in the Sepsis Syndrome"; Crit. Care Med.; 21: 1287–1295 (1993).

C. Nathan "Nitric Oxide as a Secretory Product of mammalian Cells". FASEB, 6: 3051–3064 (1992).

E. Nava, et al. "Inhibition of Nitric oxide Synthesis in Septic Shock: How Much is Beneficial?". Lancet, 338: 1555–1556 (1991).

R.M.J. Palmer "Discovery of Nitric Oxide in the Vessel Wall". A. Unifying Concept in the Pathogenesis of Species Arch. Surg., 128: 396–401 (1993).

S. Moncada, et al. "Mechanisms of Disease: The L-Arginine–Nitric Oxide Pathway" New Eng. J. 329: 2002–2012 (1993).

J. Zatarain, et al. "Vitamin B12A Prevents and Reverses Endotoxin–Mediated Hypotension and Decreases Mortality by Binding Excess Nitric Oxide" FASEB, 8: 2077 (1994).

M.A.S. Rajanayagam, et al., British Journal of Pharmacology, 108(1), pp. 3–5, 1993.

*Primary Examiner*—Raymond Henley, III
*Attorney, Agent, or Firm*—Scully, Scott, Murphy & Presser

[57] ABSTRACT

The present invention describes a method of sequestering nitric oxide from the bloodstream, endothelium or tissues of mammals by administering a cobalamin to such mammals. A method of treating diseases characterized by elevated nitric oxide levels in the bloodstream, endothelium or tissues is further provided. In particular, a method of treating sepsis by administering a therapeutic dose of hydroxocobalamin is described by the present invention. A method of alleviating systemic hypotension in a septic patient is further described by this invention. A pharmaceutical composition comprising a cobalamin in a concentration ranging from 0.5 to 50 mg composition/Kg body weight for mammals and is also provided.

16 Claims, 14 Drawing Sheets

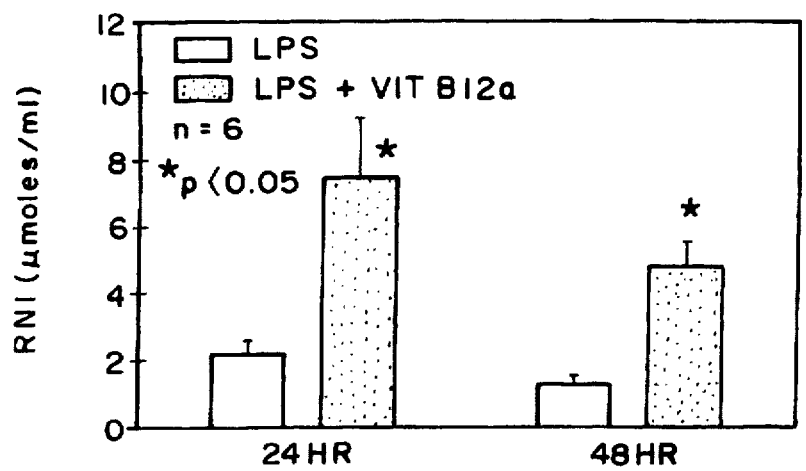
FIG.IIA
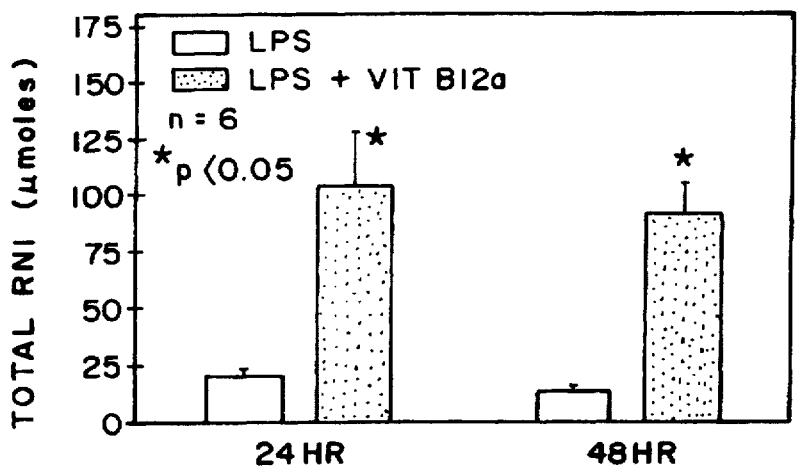
FIG.IIB
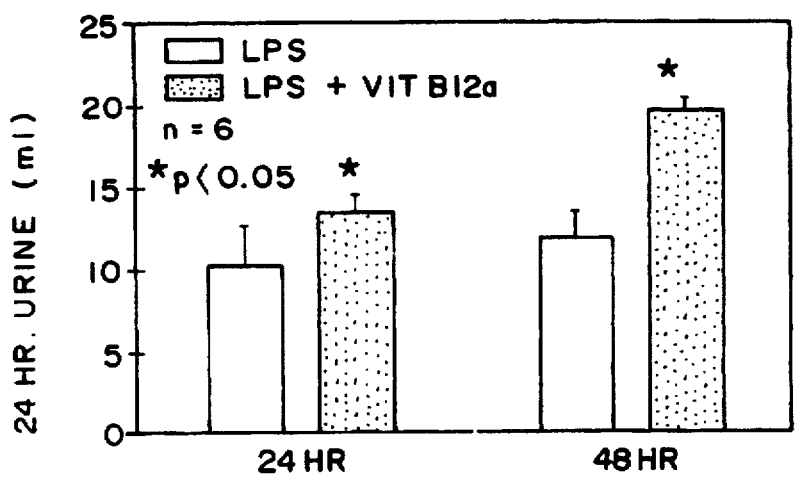
FIG.IIC

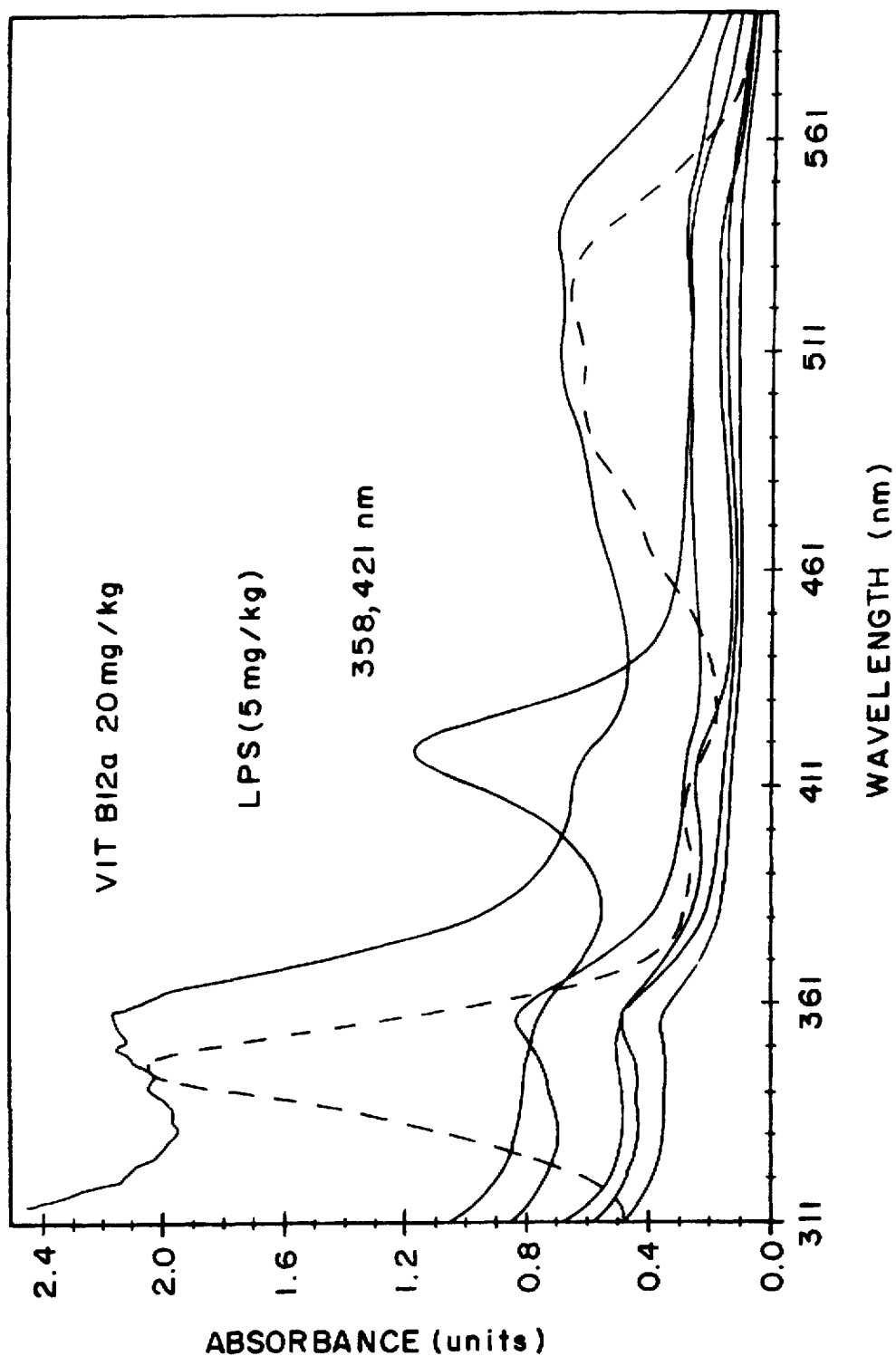

NITRIC OXIDE SEQUESTRANT

This is a 371 of PCT/US94/05650 filed May 17, 1994.

FIELD OF THE INVENTION

The present invention provides a method of sequestering nitric oxide from the bloodstream, endothelium or tissues of mammals by administering a cobalamin to such mammals. The present invention further provides a method of treating diseases in a mammal characterized by elevated nitric oxide levels in the bloodstream, endothelium or tissues of such mammals by administering a therapeutic dose of a cobalamin. In particular, the present invention describes a method of treating mammals with sepsis by administering a therapeutic dose of hydroxocobalamin. A method of reducing pathologic nitric oxide levels in mammals by administering a therapeutic dose of a cobalamin to sequester the excess nitric oxide is also described by the present invention. A method of alleviating systemic hypotension in a septic patient is further provided by the invention. A pharmaceutical composition comprising a cobalamin in a concentration ranging from 0.5 to 50 mg composition/kg body weight for mammals is also provided.

BACKGROUND OF THE INVENTION

Furchgott and Zowadzki discovered that vascular endothelium played a critical role in the regulation of vascular tone through the release of endothelium-derived relaxing factor (EDRF). Furchgott et al. (1980) *Nature* 280:373–376. In 1988, Palmer et al. concluded that EDRF was actually nitric oxide when they observed that the release of nitric oxide from the endothelial cells occurred in amounts sufficient to account for the biological activity attributed to EDRF. Palmer et al. (1987) *Nature* 327:524–526. It is now known that nitric oxide regulates a continuous vasodilator tone and thereby maintains normal homeostatic blood pressure.

A number of pathological conditions are characterized by excess nitric oxide production. Such diseases include the systemic inflammatory response syndrome (SIRS) including sepsis and septic shock; endotoxemia; GI inflammatory diseases such as ileitis, colitis and Crohn's Disease; chronic inflammatory disease; autoimmune disorders; and rheumatoid arthritis. Moncada et al. (1993) *N. Engl. J. Med.*, 329: 2002–2012. Most recently, pertussis (whooping cough) was found to be characterized by an excess production of nitric oxide. Leff (1994) *Bioworld Today*, 5:1. Various treatments, such as treating cancer with cytokines, can also lead to elevated nitric oxide levels.

The importance of understanding the role of nitric oxide in these pathological conditions is evident from the incidence and mortality rates associated with these diseases. For example, the Centers for Disease Control estimates that sepsis occurs in approximately 500,000 patients in the United States and 400,000 patients in the European community annually and is associated with a 35% mortality rate. It is the most common cause of death in noncoronary, intensive care units. With regard to GI inflammatory conditions, the Crohn's and Colitis Foundation of America estimates that 1 million people suffer from ulcerative colitis in the United States with 15,000 new cases reported annually. Further, approximately 2 million people are reported to have rheumatoid arthritis.

Nitric oxide is synthesized in mammalian cells from the amino acid L-arginine by a family of enzymes, the nitric oxide synthases, via the L-arginine-nitric oxide pathway. Moncada et al. (1993) *N. Engl. J. Med.*, 329:2002–2012. The production of nitric oxide via the nitric oxide-arginine pathway begins when a guanidine nitrogen of L-arginine undergoes a five-electron oxidation to yield the gaseous radical nitric oxide via an $N^w$-hydroxyl-L-arginine intermediate. NADPH (nicotine adenine diphosphonucleotide, reduced) donates two electrons for the formation of this intermediate and one electron for its further oxidation. Both steps are catalyzed by nitric oxide synthase. In addition to the gaseous radical nitric oxide, L-citrulline is also produced. Molecular oxygen is incorporated into both the L-citrulline and the nitric oxide formed. Tetrahydrobiopterin is required for the oxidation of the intermediate, $N^w$-hydroxyl-L-arginine, to L-citrulline. The amount of tetrahydrobiopterin required is substoichiometric with respect to the nitric oxide generated, provided that tetrahydrobiopterin can be regenerated from its oxidized form, quinonoid dihydrobiopterin.

Two distinct isozymes of nitric oxide synthase have been identified and include constitutive nitric oxide synthase (cNOS) and inducible nitric oxide synthase (iNOS). These isoforms differ in primary structure, cofactor requirements, tissue distribution and activation state.

Under basal conditions, endothelium-derived nitric oxide is produced by cNOS, a calcium- and calmodulin-dependant nitric oxide synthase. Constitutive nitric oxide synthase is controlled by cell surface receptors and can be activated by a variety of vasodilators including acetylcholine, bradykinin, histamine and adenosine. This enzyme is always present in the vascular endothelium of mammals. The interaction of acetylcholine or bradykinin with their receptors on vascular endothelium results in production of intracellular calcium which stimulates cNOS. The nitric oxide formed from L-arginine diffuses to nearby smooth muscle cells where it stimulates the soluble guanylate cyclase, resulting in enhanced synthesis of cyclic guanosine monophosphate (cGMP). The cGMP formed causes smooth muscle cells to relax. The formation of cGMP regulates physiological vascular tone, blood pressure and tissue perfusion by mediating endothelium-dependent relaxation and neural transmission.

The second isoform of nitric oxide synthase, inducible nitric oxide synthase, is calcium-independent and is not controlled by receptor-dependent mechanisms. This enzyme is induced in endothelial, vascular smooth muscle and phagocytic cells by endotoxins and various cytokines. When these cytokines interact with their respective receptors, calcium-independent nitric oxide synthase is induced. The induction of this enzyme causes prolonged nitric oxide synthesis, resulting in sustained activation of soluble guanylate cyclase. Continuous production of cGMP ultimately leads to prolonged smooth muscle relaxation, reduced responsiveness to vasoconstricting drugs, and possible tissue damage.

The synthesis of nitric oxide from L-arginine occurs in numerous cells and tissues. Examples of cells which produce nitric oxide include: neutrophils, megakaryocytes, Kupffer cells, macrophages, endothelial cells, hepatocytes, murine fibroblasts and EMT-6 cells. Examples of tissues that generate nitric oxide include: vascular smooth muscle, the brain, the adrenal gland, endocardium, peripheral and sensory nerves and the myocardium. Moncada et al. (1993) *N. Engl. J. Med.*, 329: 2002–2012.

The role of nitric oxide in the initiation of sepsis in a mammal is known in the art. Sepsis is defined as the presence of pathologic microorganisms or their toxins in the blood or other tissues of a mammal. Septic shock is shock that develops in the presence of severe infections, especially following bacteremia caused by Gram-negative bacteria and release of endotoxin. Sepsis is characterized by systemic vasodilation, a defective vascular reactivity to vasoconstrictor agents and an abnormality in microvascular regulation. Severe sepsis is associated with hypotension, organ perfusion abnormalities and other symptoms which can ultimately lead to septic shock. Septic shock is characterized by fever, vomiting, chills and nausea. As the shock progresses, heart failure, respiratory insufficiency and coma may occur. These conditions may ultimately lead to the patient's death.

Sepsis is generally caused by a Gram-negative bacterium which releases endotoxin, a complex cell-wall component of Gram-negative bacteria. Endotoxin activates iNOS to generate nitric oxide in vascular endothelium according to the L-arginine-nitric oxide pathway. Aldridge (1993) *Tibtech*, 11:373–375. Endotoxin also initiates an inflammatory response. This inflammatory response can be activated by other infectious and non-infectious stimuli.

Endotoxin contains lipopolysaccharide (LPS), a complex molecule made up of three components: lipid A, a core polysaccharide and an antigenic oligosaccharide side-chain. Lipid A of LPS binds to lipopolysaccharide binding protein (LBP) found in blood plasma. The concentration of LBP increases 100-fold due to an acute-phase response to the infection. When the LPS-LBP complex binds to the CD14 receptor on monocytes and macrophages, transcription of tumor necrosis factor (TNF) increases threefold and the translation of TNF increases 100,000-fold. In addition, the synthesis of numerous cytokines, including interleukin 1 (IL-1), IL6, IL-8 and platelet-activating factor (PAF) is initiated. These cytokines further induce nitric oxide synthase to generate nitric oxide. Lorente et al. (1993) *Crit. Care Med.* 21:1287–1295.

The release of IL-1 and IL-6 activates T cells to produce γ-interferon, IL-2, IL-4 and granulocyte-macrophage colony stimulating factor (GM-CSF). At the same time, both the complement pathway and the coagulation cascade become activated by LPS, TNF or another mediator. The complement pathway and GM-CSF, IL-2, IL-4 and γ-interferon activate neutrophils. Once activated, neutrophils adhere to the vascular endothelium which lines the heart, blood and lymph vessels.

The interaction of these biologic response modifiers results in widespread endothelial damage, and may produce hypotension, a severe fall in blood pressure, which can ultimately cause septic shock. Prolonged septic shock can lead to a deficiency in oxygen and nutrients in the tissues and a build-up of toxic metabolites resulting in tissue injury. Further, the activation of the coagulation cascade causes malfunction of the circulatory system, which can lead to multiple organ failure.

There are many therapies currently used to treat mammals with sepsis, however, each has its limitations. Until recently, the most common method of treating septic patients consisted of admininistering antibiotics and supportive therapies such as fluid replacement. The problem with this therapeutic regime was that it did not alleviate the underlying inflammation. In recent years, investigators have proposed inhibiting one of the biologic response modifiers involved to alleviate the deleterious effects of sepsis.

One method proposed to treat septic patients was to target the endotoxin released by the Gram-negative bacteria to prevent the accumulation of endotoxin from initiating the sepsis pathway. Evans et al. (1993) *J. Med. Microbiol.*, 38: 237–239. Specifically, treatment involved using a human IgM monoclonal antibody (HA-IA) against the lipid A of LPS contained in endotoxin. Clinical trials on patients with Gram-negative sepsis, however, revealed that patients treated with HA-IA had a higher mortality rate compared to patients treated with a placebo. Further, the proposed treatment was not effective against all forms of sepsis since Gram-positive sepsis can be triggered by a stimulus other than endotoxin.

A second method suggested for treating patients with sepsis was to target the biologic response modifier IL-1 with a recombinant IL-1 receptor antagonist, thereby blocking IL-1 activity within the pathogenetic sequence in sepsis. Aldridge (1993) *Tibtech*, 11: 373–375. This method of treatment, however, was not affective in alleviating the deleterious effect of sepsis. Clinical trials on patients using this therapy revealed that patients treated with an IL-1 receptor antagonist had an increased mortality rate compared to patients treated with a placebo.

Other investigators have suggested treating individuals with sepsis by inhibiting the biologic response modifier TNF using TNF inhibitors. This method of treatment overcomes one of the problems associated with the endotoxin antibody therapy in that TNF is generated regardless of whether the sepsis is initiated by a Gram-negative and Gram-positive bacteria. The problem with this treatment, however, is that TNF plays an important role in the normal response to infection. Thus, administering large amounts of anti-TNF antibody could be detrimental to a patient who does not have excessive levels of TNF. Bone (1993) *Crit. Care Med.*, 21: 311–312.

A further method of treating septic patients proposed was administering non-selective inhibitors of cNOS and iNOS. Although these treatments demonstrated a reversal of the hypotension associated with sepsis, deleterious side effects including morbidity occurred. To overcome these side effects, investigators have proposed administering nitric oxide, in the form of a nitric oxide donor compound, simultaneously with inhibitors of cNOS and iNOS. This treatment regime, however, may impair the phagocytic and bactericidal function of the phagocyte.

Other investigators have attempted to treat patients with septic shock using prepared hemoglobin (hemoprotein) combined with a pharmaceutical carrier. These investigators assert that the iron in hemoglobin binds to the free nitric oxide. The problem with this method of treatment is that it is very difficult to prepare the hemoprotein. Furthermore, since hemoprotein is a protein, the hemoprotein may act as an antigen, causing an immune response in the mammal leading to the destruction of the protein. Furthermore, previous studies have shown that cobalt binds nitric oxide more effectively than heme. Rand et al. (1993) *Clin. Exp. Pharmacol. Physiol.*, 1H: 293–296.

The present invention alleviates many of the problems associated with the current therapies for treating diseases characterized by an excess nitric oxide production. In particular, the present invention solves the problems associated with conventional therapies for sepsis, by providing a method of sequestering the excess nitric oxide using a cobalamin.

SUMMARY OF THE INVENTION

The present invention relates to a method of sequestering nitric oxide from the bloodstream, endothelium or tissues of mammals by administering a cobalamin to such mammals. In a preferred embodiment, the cobalamin is hydroxocobalamin.

The present invention further relates to a method of treating diseases in mammals characterized by elevated nitric oxide levels in the bloodstream, endothelium or tissues by administering a therapeutic dose of a cobalamin. In one embodiment, the disease is sepsis and preferred cobalamin is hydroxocobalamin.

Another aspect of this invention is directed to a method of reducing pathologic nitric oxide levels in mammals by administering a therapeutic dose of a cobalamin to sequester the excess nitric oxide.

Another aspect of this invention provides a method of alleviating systemic hypotension in a septic patient.

This invention further relates to a pharmaceutical composition comprising a cobalamin in a concentration ranging from about 0.5 to 50 mg composition/kg body weight for mammals.

Still a further aspect of this invention is directed to an article of manufacture comprising a packing material and a pharmaceutical agent contained within said packing material, wherein said packaging material comprises a label which indicates that said pharmaceutical agent is used for reducing nitric oxide levels in mammals exhibiting pathological nitric oxide levels.

BRIEF DESCRIPTION OF THE DRAWINGS

FIG. 11 shows the urinary RNI excretion 24 and 48 hours after a single intraperitoneal injection of phosphate buffered saline (PBS) or hydroxocobalamin (20 mg/kg) followed by continuous oral administration of hydroxocobalamin in the drinking water in conscious rats initially intravenously administrated 5 mg/kg of LPS.

FIG. 13 shows the U-V visual spectrum of hydroxocobalamin added to urine (dotted line) and urine from each of 6 animals treated with hydroxocobalamin and LPS.

DETAILED DESCRIPTION OF THE INVENTION

Figure 1A:
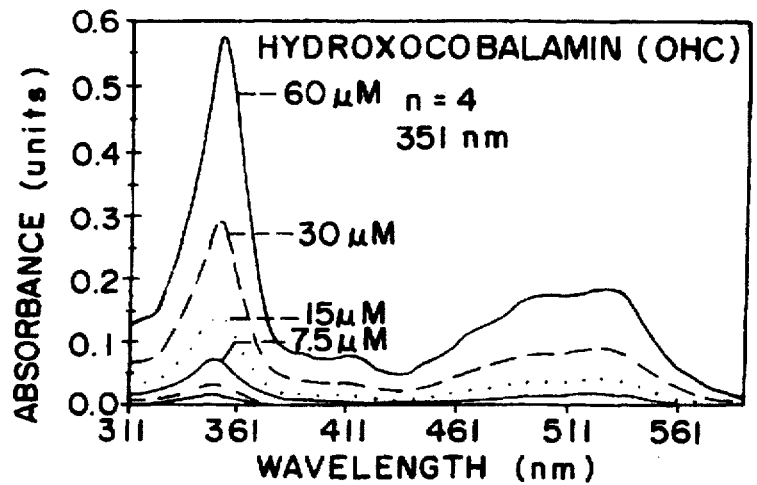
FIG. 1 shows the U-V visual spectrum of hydroxocobalamin alone (Panel A), hydroxocobalamin incubated with 55 µM of nitric oxide for 5 minutes (Panel B) and cyanocobalamin alone (Panel C).

The present invention is directed to a method of sequestering nitric oxide from the bloodstream, endothelium or tissues of mammals by administering of a cobalamin to such mammals. As defined by the present invention, the term sequester denotes removing the excess nitric oxide from the bloodstream, endothelium or tissues of mammals. In a preferred embodiment, nitric oxide is sequestered by parenterally administering a cobalamin to a mammal. In a more preferred embodiment, the cobalamin is hydroxocobalamin.

The method of the present invention utilizes cobalamins to sequester the excess nitric oxide produced in response to various pathogens and diseases in mammals. The term "cobalamins" as defined by the present invention are cobalt chelating compounds that are capable of binding to the excess nitric oxide produced. Examples of cobalamins described by the present invention include, but are not limited to, hydroxocobalamin, cyanocobalamin, transcobalamin and cobamimide.

The compounds of the present invention can be administered using any technique capable of introducing the compounds into the bloodstream of a mammal, including oral administration, and parenteral administration (e.g. intravenous, intramuscular and subcutaneous). Oral administration is feasible providing the cobalamin is resistant to digestion and passes into the blood stream.

The present invention is further directed to a method of treating diseases in mammals characterized by elevated nitric oxide levels in the bloodstream, endothelium or tissues by administering a therapeutic dose of a cobalamin. As described by the present invention, elevated levels of nitric oxide is a concentration of nitric oxide in the bloodstream, endothelium or surrounding tissue which is physiologically deleterious to said mammal.

Diseases characterized by elevated nitric oxide levels which can be treated using the method described by the present invention include: systemic inflammatory response syndrome (SIRS), including sepsis and septic shock; endotoxemia; GI inflammatory diseases such as ileitis, colitis and Crohn's Disease; chronic inflammatory disease; autoimmune disorder; rheumatoid arthritis; and pertussis.

In addition to these diseases, various treatments, including treating cancer with cytokines, often results in elevated nitric oxide levels in the body.

Numerous investigators studying the role of nitric oxide in these diseases have found that the mechanism in which nitric oxide is produced is similar. (For review see Moncada et al. (1991) *Pharm. Reviews*, 43:109–142). Therefore, the method of sequestering nitric oxide; described by the present invention can effectively be used to treat the numerous diseases characterized by an excess nitric oxide production. In a preferred embodiment, the present invention is directed to a method of treating mammals with sepsis and septic shock using a cobalamin. In a more preferred embodiment, the cobalamin is hydroxocobalamin (vitamin $B_{12a}$).

Hydroxocobalamin is a water soluble vitamin and has unique properties which enhance its clinical utility in the present invention. First, hydroxocobalamin is rapidly excreted from the body, regardless of whether it is bound or unbound to nitric oxide. Second, hydroxocobalamin possesses limited toxicity and has been clinically used, even in large doses, for many decades. Third, as a chemical sequestrant of nitric oxide, hydroxocobalamin will not affect the production of nitric oxide necessary for homeostasis. It has been demonstrated in accordance with the present invention that hydroxocobalamin when administered before or after the initiation of the hypotension associated with sepsis, the mortality rate decreases and the blood pressure returns to normal compared to untreated mammals.

A therapeutic dose of cobalamin as defined by the present invention is the amount of cobalamin necessary to bind the excess nitric oxide present in the blood stream, endothelium or tissues, thus reducing nitric oxide levels in the mammals body to alleviate or ameliorate the effects of the disease.

In a preferred embodiment, the dosage of the cobalamin administered to mammals ranges from between about 0.5 to about 50 mg compound/kg body weight. In a more preferred embodiment, the dosage of cobalamin administered to humans ranges from between about 5 to about 700 mg compound/70 kg body weight. The compounds of the present invention may be administered in a pharmaceutically-acceptable formulation using a pharmaceutical carrier, although these compounds may be administered alone. Other therapeutic agents may also be present in the formulation. In a preferred embodiment of the present invention, the cobalamins are administered parenterally.

A pharmaceutically-acceptable carrier as defined by the present invention includes, for example, a diluent that permits delivery of the active compounds without introducing undesirable side effects. The pharmaceutical carrier in which the compounds are suspended or dissolved may be any solvent or solid that is non-toxic to the mammal and compatible with the compound. Suitable pharmaceutical carriers include liquid carriers, such as normal saline or other non-toxic salts at or near physiological concentrations, and solid carriers, such as talc or sucrose.

The method of treating hypotension in a septic patient described by the present invention solves many of the problems associated with conventional therapeutic techniques for treating sepsis and septic shock. Unlike the therapies described in the prior art, the method of treating sepsis described by the present invention is easy to administer, is effective in treating sepsis regardless of the stimulus which initiates the disease, and does not result in adverse side effects associated with conventional sepsis therapy.

The present invention is further directed to a method of reducing pathologic nitric oxide levels in mammals by administering a therapeutic dose of a cobalamin to sequester the excess nitric oxide. Pathologic nitric oxide levels as defined by the present invention are elevated nitric oxide levels in the blood stream, endothelium or tissues which are physiologically deleterious to said mammal. Pathologic nitric oxide levels occurs when inducible nitric oxide synthase is expressed in mammal tissues resulting in nitric oxide production in mammalian cells at a rate that is deleterious to the mammal.

It has been discovered in accordance with the present invention that the administration of hydroxocobalamin to a mammal at a concentration of about 20 mg/kg either prior to or after endotoxin-derived lipopolysaccharide resulted in a significant attenuation of the LPS-induced hypotension. This effect was associated with increased urine volume and urinary RNI excretion and a decrease in plasma RNI. This suggests the hydroxocobalamin binds to the excess nitric oxide in the blood and excretes it from the body. In accordance with the present invention, systemic hypotension is alleviated by the administration of cobalamins.

In a preferred embodiment, the present invention contemplates administering an effective amount of hydroxocobalamin to a septic patient to treat the effects of the disease.

The present invention further contemplates an article of manufacture comprising a packing material and a pharmaceutical agent contained within said packaging material, wherein said pharmaceutical agent is effective for reducing nitric oxide levels in mammals with pathologic nitric oxide levels and wherein said packaging material comprises a label which indicates that said pharmaceutical agent can be used for reducing levels in mammals with pathological levels. The packing material used to contain the pharmaceutical agent can comprise glass, plastic, metal or any other suitably inert material.

In order to further illustrate the present invention, the experiments described in the following examples were carried out. It should be understood that the invention is not limited to the specific examples or the details described therein. The results obtained from the experiments described in the examples are shown in the accompanying FIGS. 1–13.

EXAMPLE 1

Figure 1B:
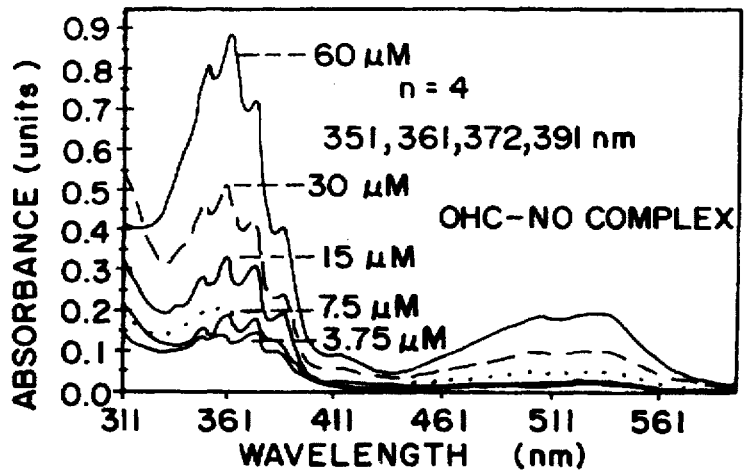
Figure 1C:
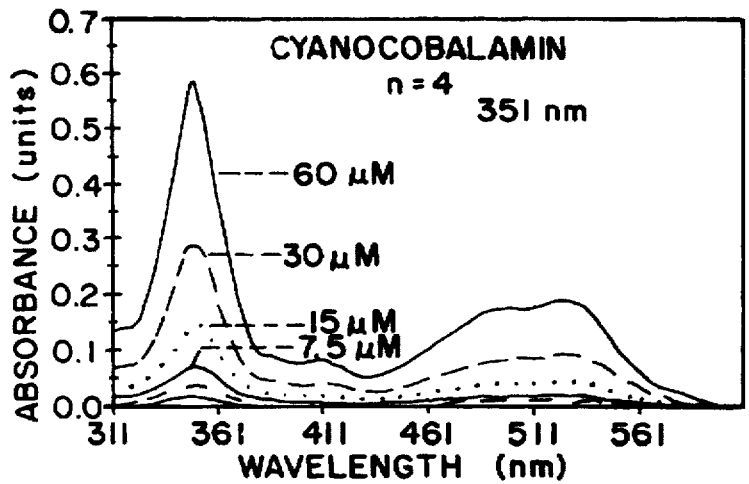

The ultraviolet visual spectrum of hydroxocobalamin, hydroxocobalamin incubated with 55 µm of nitric oxide for 5 minutes and cyanocobalamin were obtained. The concentration of hydroxocobalamin and cyanocobalamin from 7.5 µm to 60 µm were also compared. FIG. 1 shows the UV visual spectrum of hydroxocobalamin, the hydroxocobalamin-nitric oxide complex and cyanocobalamin. Both hydroxocobalamin and cyanocobalamin demonstrated single peaks at 351 nm of the vitamin concentration as shown in Panels A and C respectively of FIG. 1. When nitric oxide was added to hydroxocobalamin, four peaks at 351, 361, 372 and 391 nm were observed. This example illustrates that four isomers of hydroxocobalamin are detectable using UV visual spectrum.

EXAMPLE 2

Figure 2:
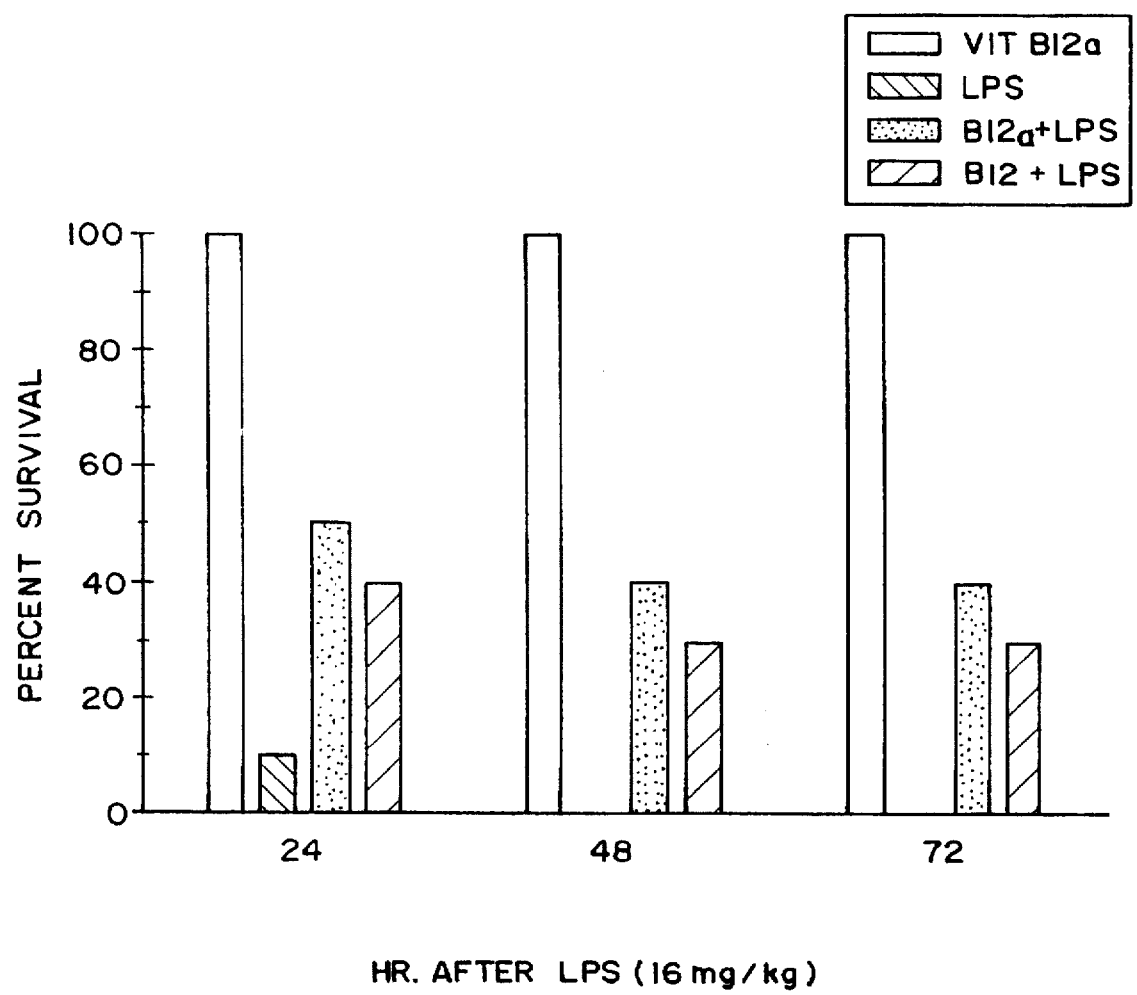
FIG. 2 shows the effect of an intraperitoneal administration of hydroxocobalamin and cyanocobalamin (20 mg/kg) on the morality rate of mice injected with a lethal injection of $E.\ coli$ endotoxin lipopolysaccharide (LPS) immediately after an injection of phosphate buffered saline (LPS control), hydroxocobalamin (vit. $B_{12a}$+LPS) or cyanocobalamin (vit. $B_{12}$+LPS). The mortality rate was monitored for 72 hrs.
Figure 3:
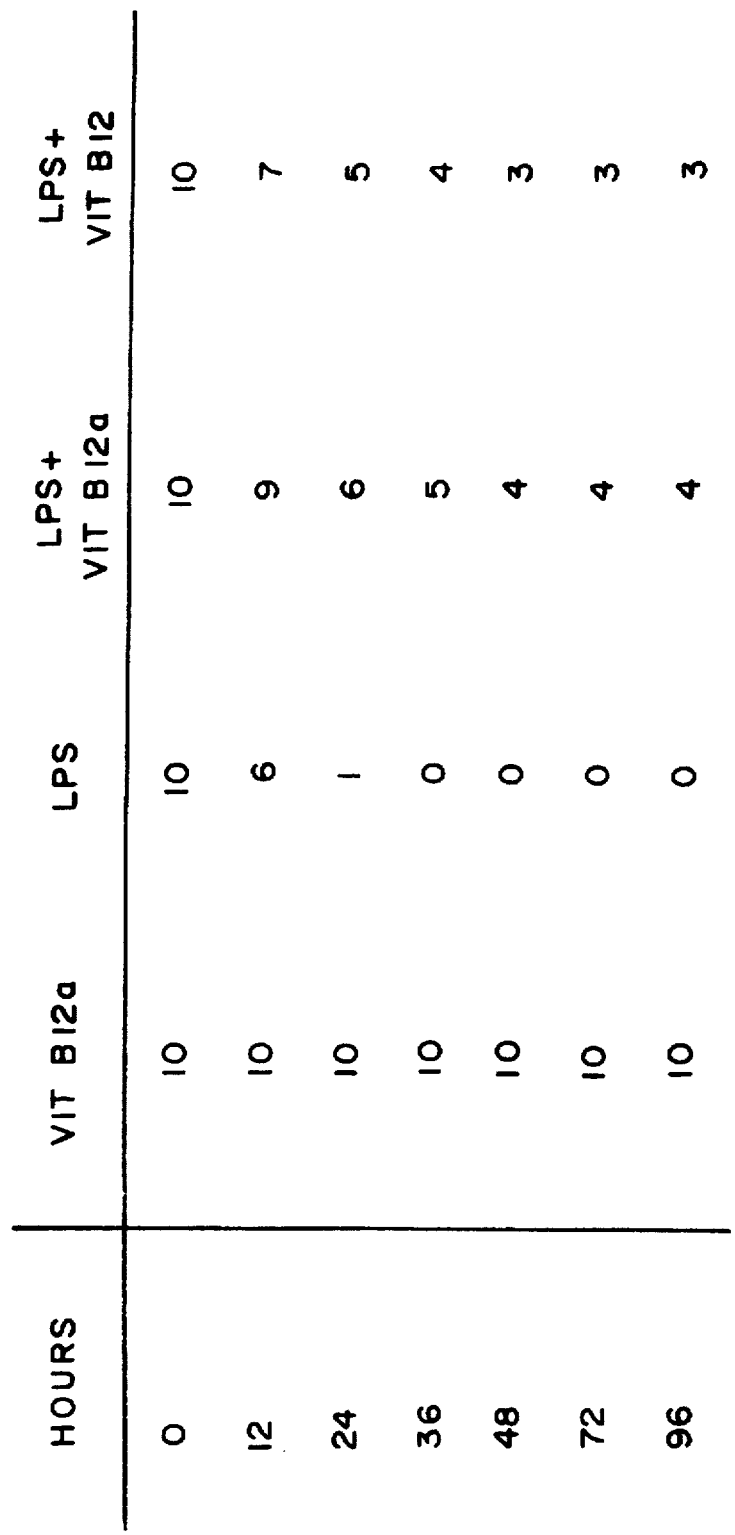
FIG. 3 shows the mortality rate of the mice depicted in FIG. 2 monitored for 96 hrs.

This study examined the effect of hydroxocobalamin (vitamin $B_{12a}$) and cyanocobalamin (vitamin $B_{12}$) on the mortality rate of 100 male, Swiss-Webster mice with LPS-induced hypotension. There were 10 mice in each group weighing between 20–22 g. The animals were given an injection intraperitoneal with either PBS (10 mg/kg body weight), vitamin $B_{12a}$ (12 mg/kg body weight) or vitamin $B_{12}$ (10 mg/kg body weight) 5 min before intraperitoneal administration of either PBS or LPS (16 mg/kg body weight). FIG. 2 shows the percentage of mice to survive 24, 48 and 72 hours subsequent to an injection of PBS only, LPS only, vitamin $B_{12a}$ and LPS, or vitamin $B_{12}$ and LPS. FIG. 3 shows the mortality rate of the mice 96 hours after their injections. One hundred percent mortality was seen by 36 hours in animals that received only LPS. As shown in FIGS. 2 and 3, for those animals that received hydroxocobalamin or cyanocobalamin 5 min. prior to the intraperitoneal administration of LPS, a survival rate of 40% or 30% respectively from 48 to 96 hours was seen. This study demonstrates that cobalamins, and in particular hydroxocobalamin and cyanocobalamin have the capacity to reduce endotoxin derived LPS induced mortality in mammals.

EXAMPLE 3

This study examined the ability of vitamin $B_{12a}$ to reverse the hypotension in rats when administered prior and subsequent to a dose of LPS. All experiments were conducted under a protocol approved by the Institutional Animal Care and Use Committee of the Louisiana State University Medical Center at New Orleans. All animals were treated according to the Guiding Principles for Laboratory Animal Care of the American Physiologic Society.

Figure 4:
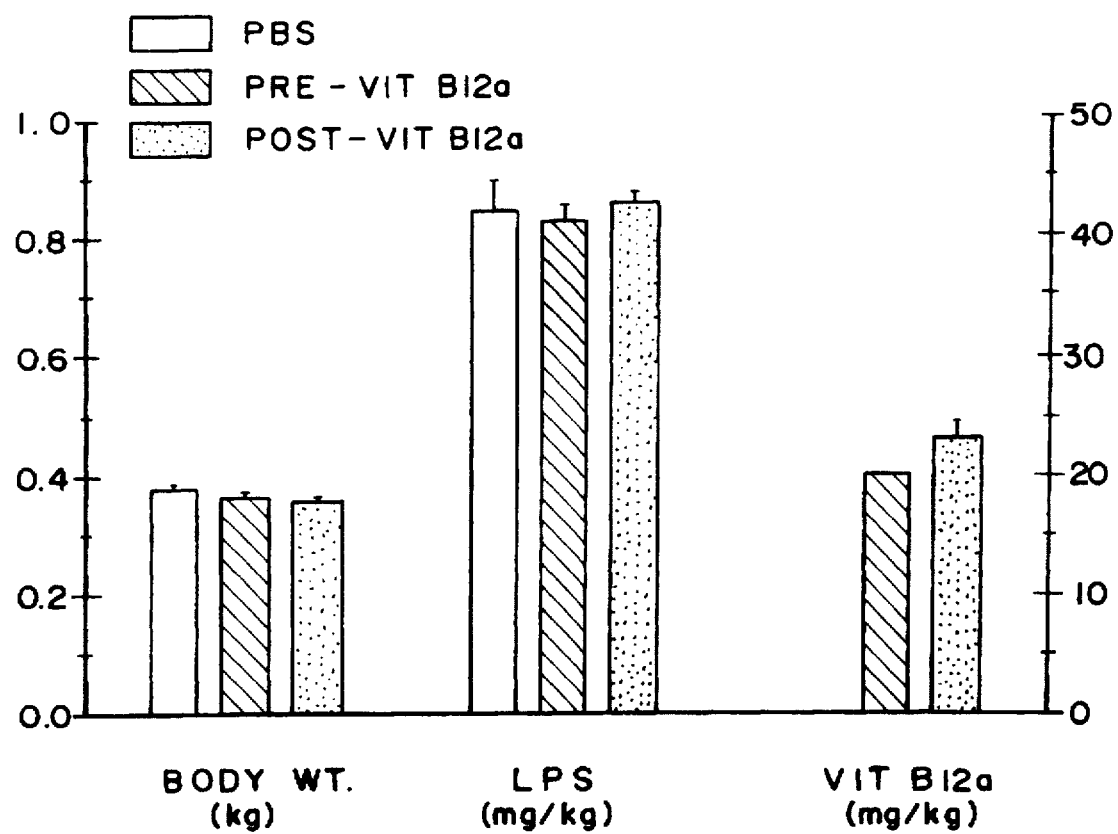
FIG. 4 shows the body weights (kg) and the amounts of LPS (mg/kg) and hydroxocobalamin (Vit. $B_{12a}$) given to rats administered phosphate buffered saline (PBS) or hydroxocobalamin (Vit. $B_{12a}$) 15 min before (Pre-Vit. $B_{12a}$) or 15 min after (Post-Vit. $B_{12a}$) administration of LPS. The ordinate is the absolute value of the parameters under study.

Male, Sprague-Dawley rats weighing between 290 to 375 g were anesthetized intramuscularly with ketamine-xylazine (25 mg/kg). Catheters were inserted into the carotid artery and jugular vein to measure blood pressure and for drug administration, respectively. After a 30 min equilibration period, the rats were intravenously administered either phosphate buffered saline solution (PBS) (0.01 ml/100 g) or vitamin $B_{12a}$ (20 mg/kg). Fifteen minutes later the rats were given intravenously either LPS (0.9 mg/kg) or PBS (0.01 ml/100 g). Endotoxin-derived lipopolysaccharide was administered to induce hypotension in the animals. FIG. 4 shows the amounts of LPS, PBS and vitamin $B_{12a}$ given during this experiment. The body weights of three groups of rats was also calculated. This figure illustrates that these experimental parameters were essentially equivalent for the three groups.

Figure 5:
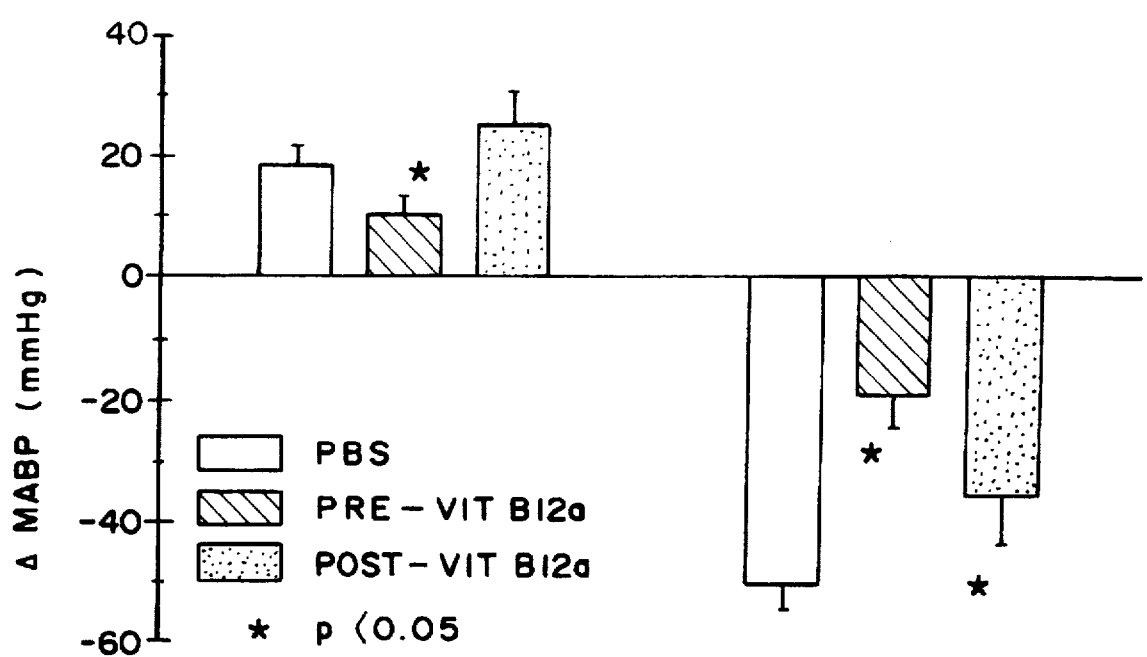
FIG. 5 shows the enhanced mean arterial blood pressure (MABP, mmHg) in rats treated intravenously with hydroxocobalamin (Vitamin $B_{12a}$) 15 minutes before (Pre-Vit. $B_{12a}$) or 15 minutes after (Post-Vit. $B_{12a}$) administration of LPS compared to the control group treated with PBS 15 minutes before or 15 minutes after the administration of LPS.
Figure 6A:
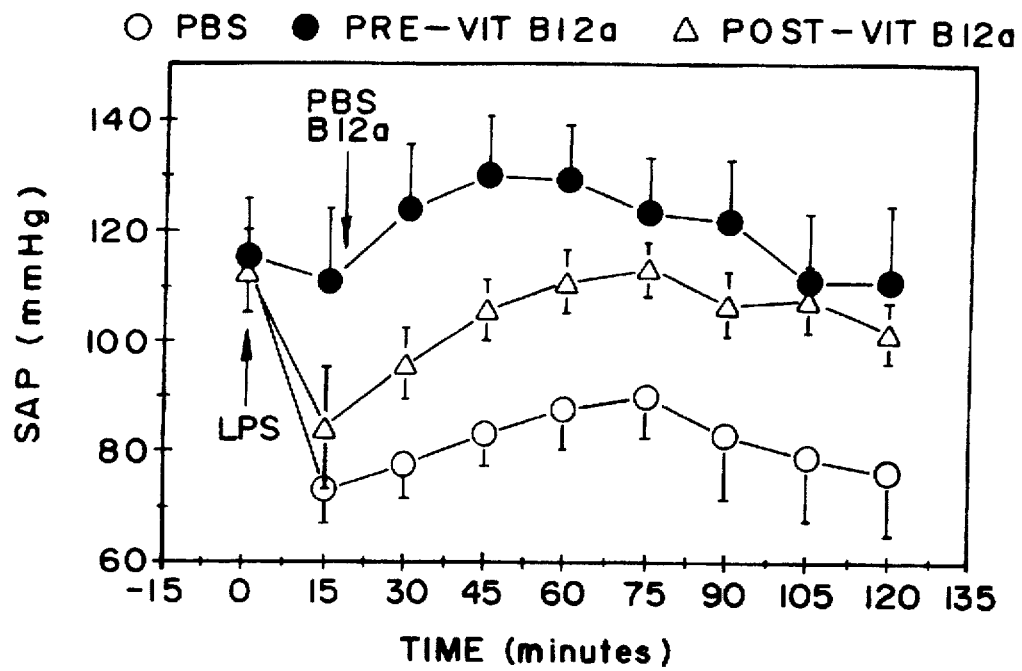
FIG. 6 shows the enhanced systolic, diastolic and mean arterial pressures of ketamin-anesthetized rats intravenously administered phosphate buffered saline (PBS) or hydroxocobalamin (Vit. $B_{12a}$) 15 minutes before (Pre-Vit. $B_{12a}$) or 15 minutes after (Post-Vit. $B_{12a}$) administration of LPS (0.9 mg/Kg).
Figure 6B:
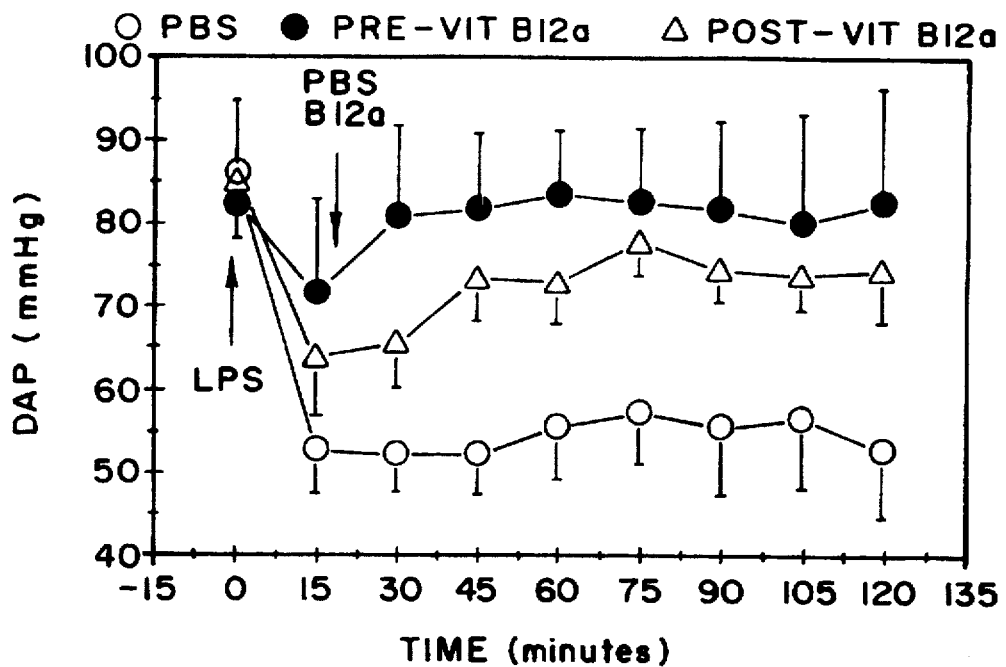
Figure 6C:
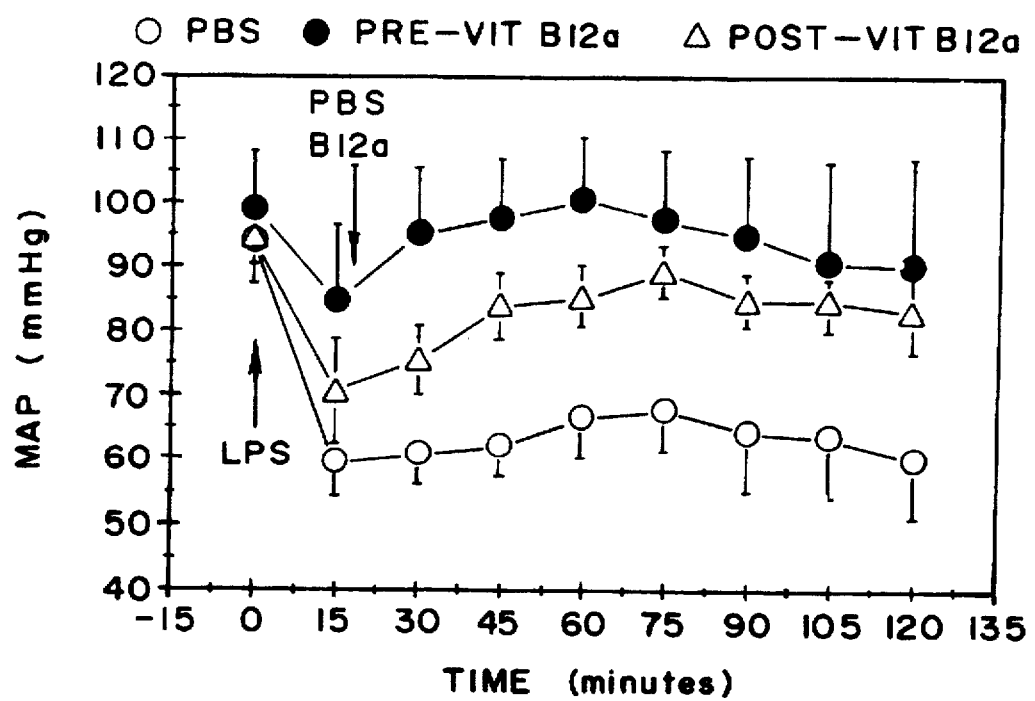
Figure 7:
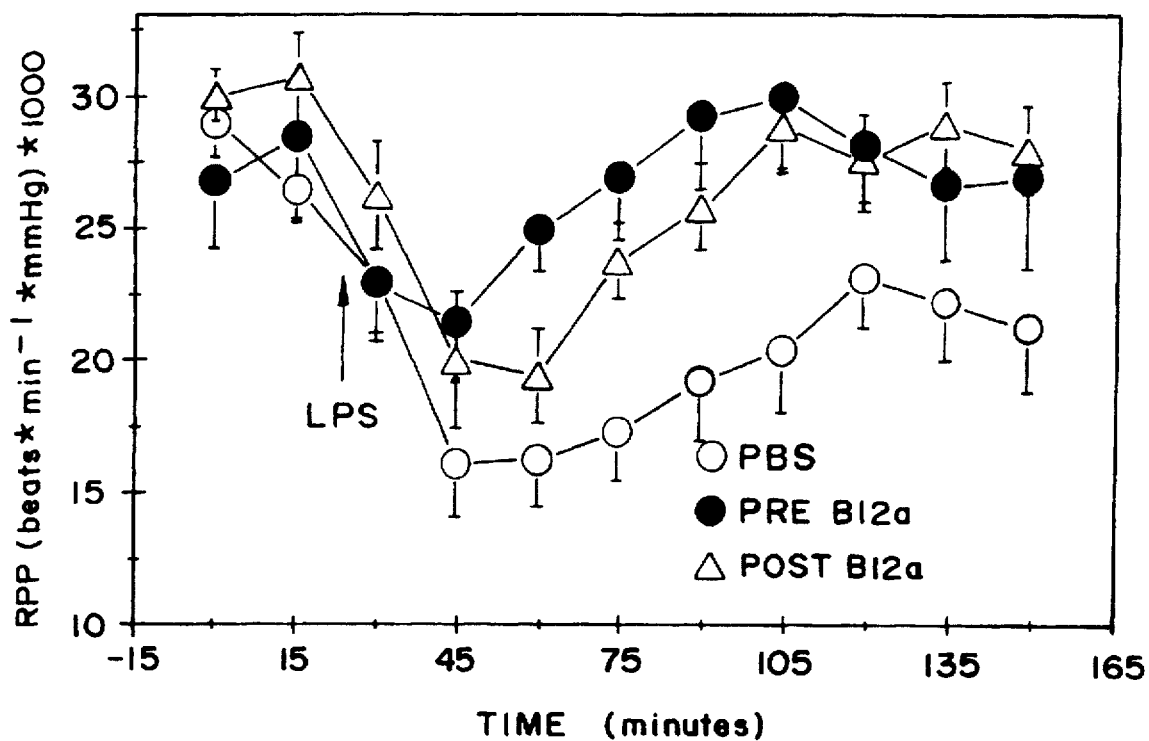
FIG. 7 shows the enhanced rate pressure product (heart rate×mean arterial systolic blood pressure) reflective of myocardial oxygen consumption and coronary blood-flow, of the ketamin anesthetized rat (Pre $B_{12a}$) following phosphate buffered saline (PBS) or hydroxocobalamin (Vit. $B_{12a}$) 15 minutes before (Pre-Vit. $B_{12a}$) or 15 minutes after (Post-Vit. $B_{12a}$) administration of LPS (0.9 mg/Kg). The ordinate is the absolute rate pressure product (beat min $^{-}$mm Hg)*1000. The abscissa is the time of the experiment.
Figure 8:
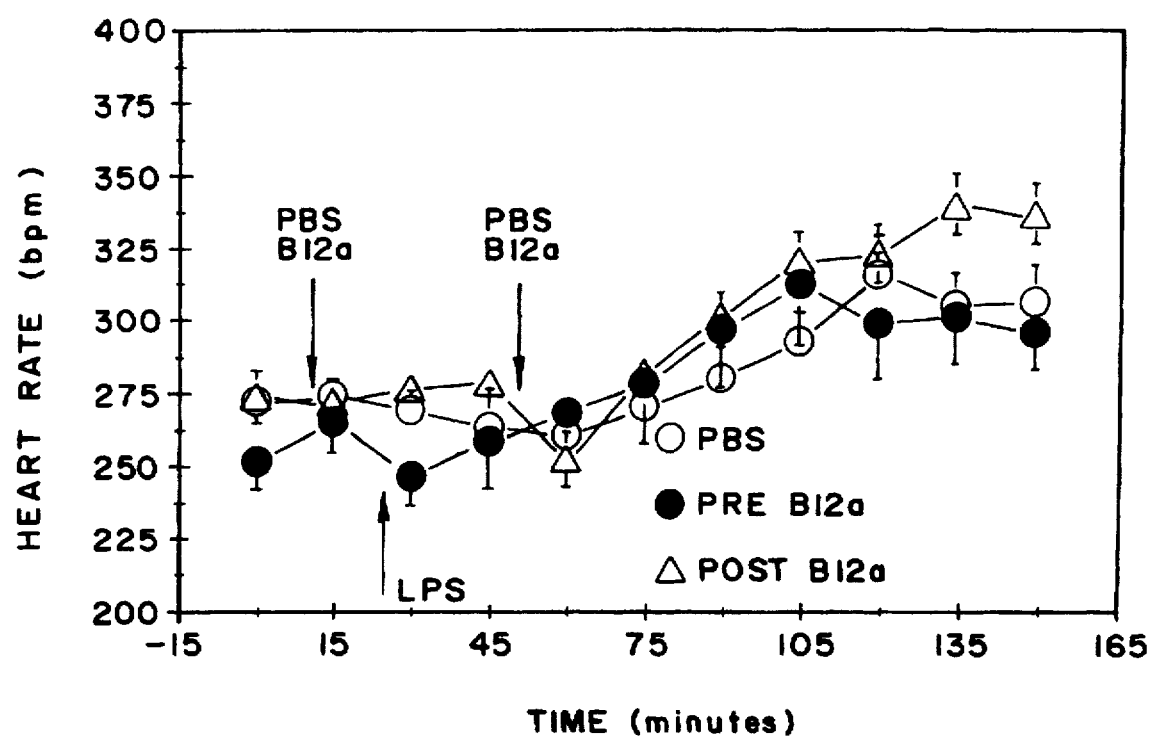
FIG. 8 shows the heart rate of the ketamin-anesthetized rat to LPS (0.9 mg/kg, iv) following phosphate buffered saline (PBS) or hydroxocobalamin (Vit. $B_{12a}$) 15 minutes before (Pre-Vit. $B_{12a}$) or 15 minutes after (Post-Vit. $B_{12a}$) administration of LPS (0.9 mg/Kg). The ordinate is the absolute heart rate at the time of administration of LPS.

In a separate group of rats, the animals were pre-treated with PBS (0.01 ml/100 g) 15 min prior to the intravenous administration of LPS. Fifteen minutes following the administration of LPS, the animals were treated intravenously with either PBS or vitamin $B_{12a}$ (20–30 mg/kg). Blood pressure and heart rate were measured using conventional techniques. FIG. 5 shows the reduction in the mean arterial blood pressure (MABP) in rats treated intravenously with hydroxocobalamin 15 minutes before and 15 minutes after administration of LPS. As shown in FIG. 5, the administration of vitamin $B_{12a}$ before and after the administration of LPS attenuated the hemodynamic response to LPS. FIG. 6 shows systolic, diastolic and mean arterial pressures of rats following the pre and post-treatment with hydroxocobalamin compared to phosphate buffered saline. This figure shows that following the administration of LPS, an initial decrease in the systolic, diastolic mean arterial pressures occurred with the first five minutes followed by a trough 10–17 minutes later. The groups that received hydroxocobalamin before or after the administration of LPS had a significant attenuation of the trough ($p<0.05$). FIG. 7 shows the rate pressure product reflective of myocardial oxygen consumption and coronary blood flow of the rats pre-and post-treatment with PBS or hydroxocabalamin. FIG. 8 shows the heart rate for the same group of animals. These results show that hydroxocabalamin attenuated the LPS-induced hypotension in mammals.

Hemodynamic parameters were continuously recorded the next two hours. After the two hour monitoring period, a thoracotomy was performed and blood (8–10 ml) was obtained by cardiac puncture. The blood was collected in polypropylene tubes and assayed for the reactive nitrogen intermediates nitrate and nitrate anions (RNI) using the following procedures.

Ten microliters of urine or plasma were added to 100 ml of a reducing solution (2.3% vanadium chloride in 2N HCl at 100° C.) under a stream of nitrogen gas. Quantification of the nitric oxide formed from RNI was determined from the specific chemiluminescence resulting from the reaction of the generated nitric oxide with ozone using a Dasibi Model 821 Nitric Oxide-NOX Analyzer (Dasibi Environmental Inc., Glendale, Calif.). The total volume of gas in the purge chamber which contained the RNI-derived nitric oxide in nitrogen was taken up by vacuum into a Dasibi Model 803 nitric oxide and $NO_x$ analyzer (Dasibi, Inc. Glendale, Calif.). This analyzer measures dissolved nitric oxide and nitric oxide derived from $NO_2$- and $NO_3$- in the incubate which has been generated by the reducing solution and stripped from the solution using the inert carrier gas (nitrogen).

The nitric oxide reacts with machine generated ozone to form excited nitric oxide which releases light at 6,500–6,800 Å, in the red region. The amount of light generated is concentration dependent and is measured with a photomultiplier tube. The lowest reproducible limit of detection of nitric oxide when corrected for background was 7 picomoles using 10 μl injectates and standard solutions of $NO_2$- and $NO_3$- prepared fresh daily and treated in a manner identical to the samples. The extent of conversion of $NO_2$- and $NO_3$- to nitric oxide was 94.8±0.1% (n=124) when compared with standard solutions of nitric oxide and nitric oxide calibration gases.

In both studies, the urine volume of the animal was measured by compressing the bladder until it was emptied. The urine was collected in calibrated centrifuge tubes on ice. The bladder was tied off with surgical suture, removed from the animal and any remaining urine was added to the urine collected calibrated centrifuge tubes on ice. The volume of urine was recorded and frozen at −80° C. until assayed for RNI.

Figure 9:
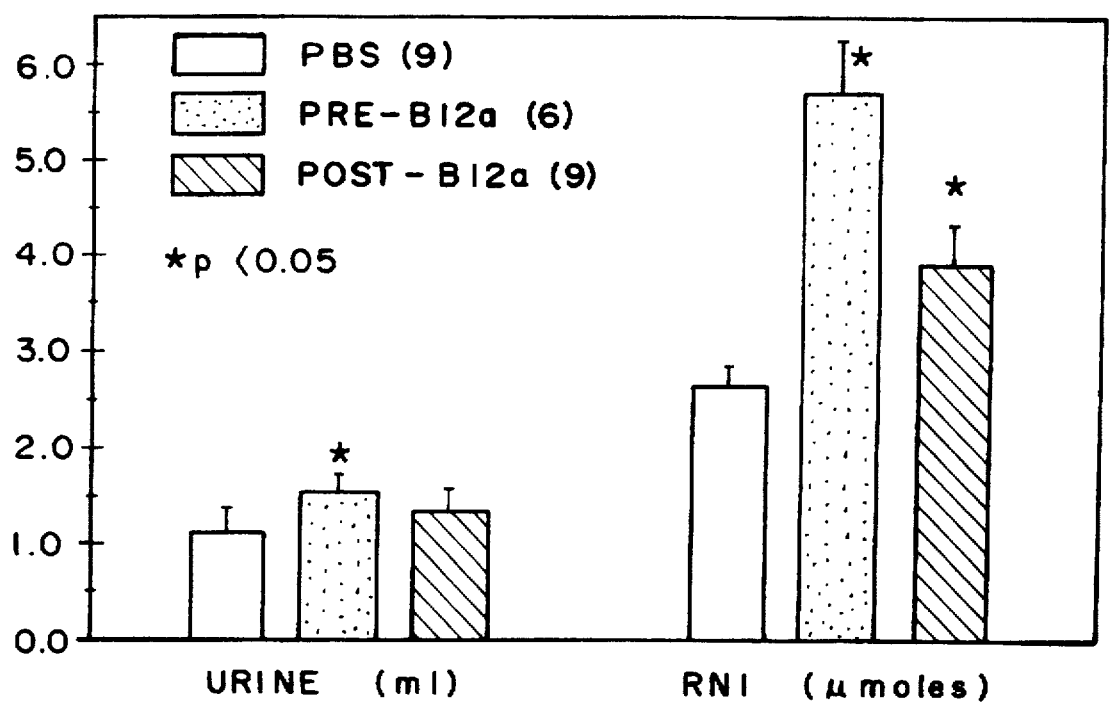
FIG. 9 shows the enhanced urinary excretion and urine concentration of nitrite and nitrate (RNI) following phosphate buffered saline (PBS) or hydroxocobalamin (Vit. $B_{12a}$) 15 minutes before (Pre-Vit. $B_{12a}$) or 15 minutes after (Post-Vit. $B_{12a}$) administration of LPS (0.9 mg/Kg). The ordinate is the bladder urine volume in ml or the total RNI content in µmoles.
Figure 10:
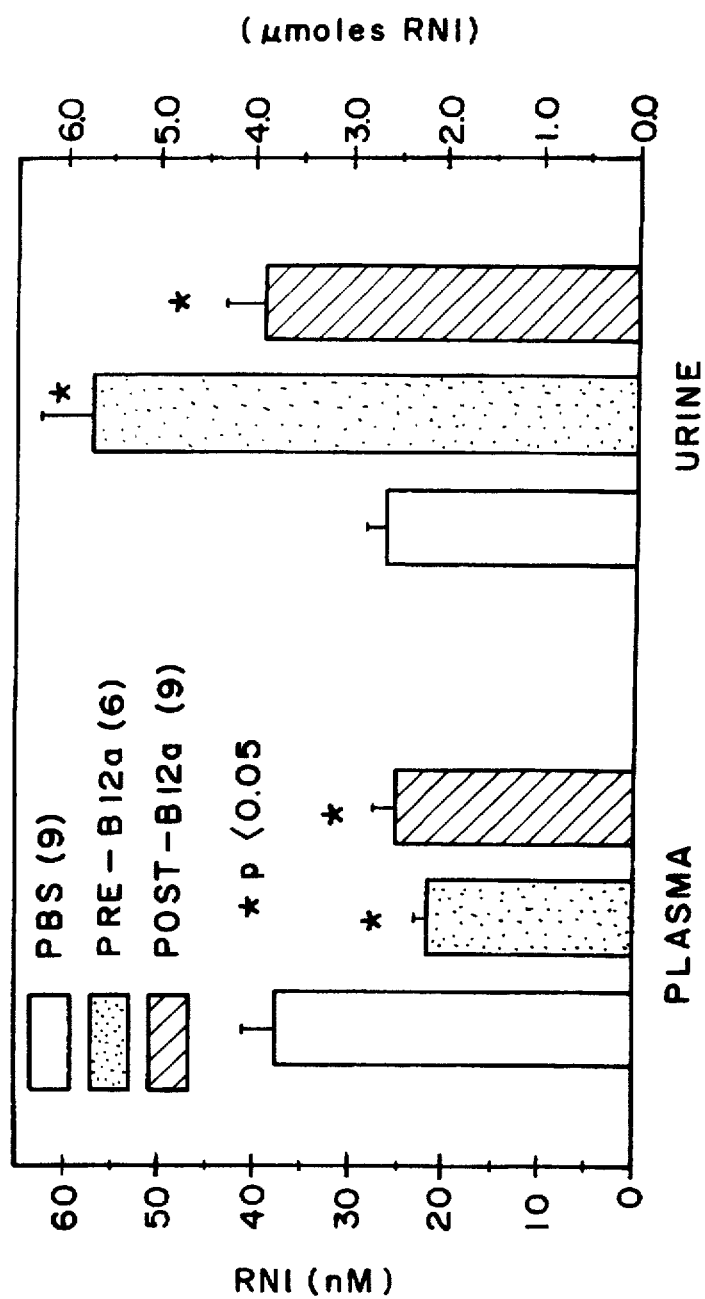
FIG. 10 shows the enhanced urine concentration and the reduced plasma concentration of nitrite and nitrate (RNI) following phosphate buffered saline (PBS) or hydroxocobalamin (Vit. $B_{12a}$) 15 minutes before (Pre-Vit. $B_{12a}$) or 15 minutes after (Post-Vit. $B_{12a}$, administration of LPS. The ordinate is the bladder urine volume in ml or the total RNI content in µmoles.
Figure 12:
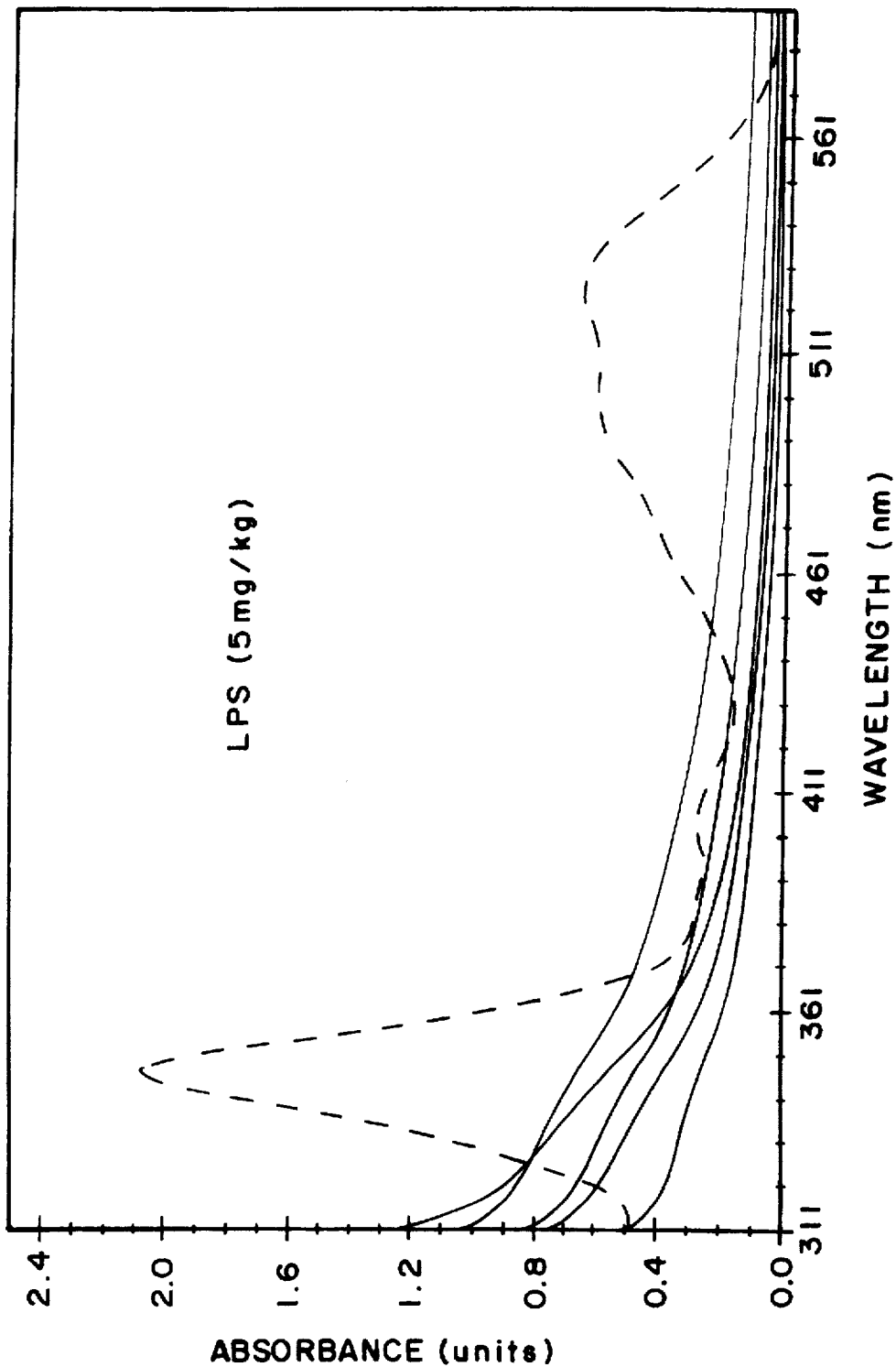
FIG. 12 shows the U-V visual spectrum of hydroxocobalamin added to urine (dotted line) and urine from each of 6 animals treated with LPS.

FIG. 9 shows the enhanced urine concentration of RNI following a pre-and post-treatment with hydroxocabalamin compared to treatment with PBS for LPS-induced hypotension rats. As illustrated by FIG. 10, vitamin $B_{12a}$ enhanced LPS-induced urinary RNI excretion and decreased elevated plasma RNI. These results suggest that hydroxocabalamin birds to nitric oxide in the bloodstream, endothelium or tissues, thereby reducing the concentration of RNI in the plasma and enhances the urinary excretion of RNI, thereby limiting its deleterious effect on the vascular system.

EXAMPLE 4

These studies analyzed whether vitamin $B_{12a}$ administered to conscious rats with LPS induce hypotension would increase the excretion of RNI and form a nitric oxide-hydroxocobalamin complex. Vitamin $B_{12a}$ (20 mg/kg) was administered intravenously followed by an intraperitoneal administration of LPS (5 mg/kg) or PBS (0.1 ml/100 g) to rats housed in metabolic cages. Urine was collected under mineral oil, in light resistant containers every 24 hr. over the next 72 hr. Rats were allowed food and water or food and water containing vitamin $B_{12a}$ to provide approximately an additional 20 mg/kg/day of vitamin $B_{12a}$. Total urinary RNI and the ultraviolet-visual spectrum of the hydroxocobalamin in the urine was measured.

FIG. 11 shows that vitamin $B_{12a}$ alternates and prevents LPS-induced hypotension in unanesthetized rats. The UV-visual spectrum show that when hydroxocobalamin was added to the urine of the mammals treated with hydroxocobalamin and LPS, a complex with nitric oxide was formed.

We claim:

1. A method of treating a disease in a mammal characterized by elevated nitric oxide levels in the bloodstream, endothelium or tissues of said mammal, said disease selected from the group consisting of systemic inflammatory response syndrome, sepsis, septic shock, endotoxemia and pertussis consisting essentially of administering to a mammal in need thereof a therapeutic dose of a cobalamin to sequester the excess nitric oxide.

2. The method of claim 1 wherein said cobalamin is selected from the group consisting of hydroxocobalamin (Vitamin $B_{12a}$), cyanocobalamin (Vitamin $B_{12}$), transcobalamin or cobamimide.

3. The method of claim 1 wherein said cobalamin is hydroxocobalamin.

4. The method of claim 1 wherein said cobalamin is administered parenterally.

5. The method of claim 1 wherein said cobalamin is administered at a concentration ranging from 0.5 to 50 mg compound/kg body weight in a mammal.

6. The method of claim 1 wherein said cobalamin is administered at a concentration ranging from 5 to 700 mg compound/70 kg body weight in a human.

7. The method of claim 1 wherein said disease is the systemic inflammatory response syndrome.

8. The method of claim 1 wherein said disease is sepsis.

9. The method of claim 1 wherein said disease is septic shock.

10. The method of claim 1 wherein said disease is endotoxemia.

11. A method of alleviating systemic hypotension in a septic patient comprising administering an effective amount of a cobalamin to sequester the excess nitric oxide produced.

12. The method of claim 11 wherein said cobalamin is selected from the group consisting of hydroxocobalamin, cyanocobalamin, transcobalamin or cobamamide.

13. The method of claim 11 wherein said cobalamin is hydroxocobalamin.

14. The method of claim 11 wherein said cobalamin is administered parenterally.

15. The method of claim 11 wherein said cobalamin is administered at a concentration ranging from 5 to 700 mg compound/70 kg body weight to said septic patient.

16. A method of treating a disease in a mammal characterized by elevated nitric oxide levels in the bloodstream, endothelium or tissues of said mammal, comprising administering to a mammal in need thereof a therapeutic dose of a cobalamin to sequester the excess nitric oxide, wherein said disease is pertussis.

* * * * *